United States Patent [19]

Pawloski et al.

[11] Patent Number: 4,945,118
[45] Date of Patent: Jul. 31, 1990

[54] (HALONEOCARBYL-SUBSTITUTED)(ALIPHATIC OR OXYALIPHATIC)(HALOGENATED ALIPHATIC OR OXYALIPHATIC)-PHOSPHORATES WITH POLYURETHANES

[75] Inventors: Chester E. Pawloski, Bay City; Donna J. Fielding; David J. Wampfler, both of Midland, all of Mich.

[73] Assignee: The Dow Chemical Company, Midland, Mich.

[21] Appl. No.: 347,097

[22] Filed: May 3, 1989

Related U.S. Application Data

[62] Division of Ser. No. 895,541, Aug. 11, 1986, Pat. No. 4,851,559.

[51] Int. Cl.$^5$ .............................................. C08G 18/14
[52] U.S. Cl. .................................... 521/107; 521/906; 524/144; 524/712
[58] Field of Search ................ 521/107, 906; 524/144, 524/712

[56] References Cited

U.S. PATENT DOCUMENTS

| Re. 24,514 | 7/1958 | Hoppe et al. | 260/2.5 |
|---|---|---|---|
| 2,846,408 | 9/1958 | Brachhagen et al. | 260/2.5 |
| 2,871,219 | 10/1959 | Baggett et al. | 260/45.85 |
| 2,891,073 | 2/1959 | Smith | 260/340.2 |
| 3,058,921 | 3/1962 | Pannell | 260/2 |
| 3,132,169 | 12/1964 | Birum et al. | 558/202 |
| 3,324,205 | 7/1967 | Carpenter et al. | 558/104 |
| 3,755,212 | 8/1973 | Dunlap et al. | 260/2.5 |
| 3,784,500 | 9/1974 | Gibbons | 260/30.4 |
| 3,821,130 | 4/1974 | Barron et al. | 260/2.5 |
| 3,849,146 | 11/1974 | Walters et al. | 90/107 |
| 3,928,299 | 3/1975 | Rosenkranz et al. | 260/875 |
| 4,046,719 | 11/1977 | Stanaback et al. | 260/2.5 |
| 4,083,825 | 3/1978 | Albright et al. | 558/298 |
| 4,101,470 | 4/1978 | McEntire | 521/118 |
| 4,433,170 | 5/1984 | Zimmerman et al. | 564/505 |
| 4,450,246 | 7/1984 | Jachimowicz | 521/129 |
| 4,464,488 | 10/1984 | Zimmerman et al. | 521/115 |

OTHER PUBLICATIONS

Kohler et al., *J. Am. Chem. Soc.,* 49 3181–88 (1927).
ANSI/ASTM D-2863-77
German DIN-4102-B2.
ASTM E-84.
Cal. Tech. Bull. 117, State of Cal. Dept. of Consumer Affairs Bureau of Hom Furnishings, N. Highlands, Calif. (Jan. 1980).

*Primary Examiner*—Maurice J. Welsh
*Attorney, Agent, or Firm*—Paula Sanders Ruhr

[57] ABSTRACT

Included are the title phosphorate compounds, and a process to prepare them comprising contacting a carbylphosphorate mono acid halide with a carbyloxide. For example, ((2-(3-bromo-2,2-bis(bromomethyl)-propoxy)ethyl(choroethyl)-(ethyl))phosphorate can be prepared with (2-(3-bromo-2,2-bis(bromomethyl)propoxy)ethyl)(ethyl)-chloridophosphorate and ethylene oxide. The compounds are useful so-called flame-retardants for polyurethanes, especially flexible foams because, for example, substantially non-scorching and non-odoriferous flame-retardant flexible foams can be readily prepared with the compounds.

12 Claims, No Drawings

(HALONEOCARBYL-SUBSTITUTED)(ALIPHATIC OR OXYALIPHATIC)(HALOGENATED ALIPHATIC OR OXYALIPHATIC)-PHOSPHORATES WITH POLYURETHANES

This is a divisional of application Ser. No. 895,541, filed Aug. 11, 1986, now U.S. Pat. No. 4,851,559.

FIELD

The invention concerns organic phosphorous compounds, their preparation and use. The use particularly concerns flame-retarding compositions such as polyurethanes, for example, flexible foams, which are useful structural materials, for example, in insulating and upholstery cushioning.

BACKGROUND

Carpenter et al., U.S. Pat. No. 3,324,205 (1967), discloses certain chlorinated or brominated quaternary carbon moiety-containing phosphates. These phosphates are disclosed to be useful for imparting flame-resistance to certain normally flammable organic materials.

A problem in the art is production of highly marketable polyurethanes, particularly flexible foams and especially as slabstock. Therein, scorch, odor, processability and flame-retardant efficiency are among production characteristics often needing improvement.

SUMMARY

The invention, in one aspect, is a novel (haloneocarbyl-substituted)(aliphatic or oxyaliphatic)(halogenated aliphatic or oxyaliphatic)phosphorate. Another aspect is a process to prepare said phosphorate comprising contacting a carbylphosphorate mono acid halide with a carbyloxide under conditions whereby said phosphorate is prepared. Still another aspect is a use of said phosphorate in a method for satisfying a production characteristic of a flame-retardant polyurethane comprising incorporating said phosphorate into polyurethane under conditions whereby said characteristic is satisfied. A further aspect is a process to prepare a flame-retardant polyurethane comprising reacting a polyahl with an organic isocyanate in the presence of said phosphorate. An additional aspect is flame-retardant polyurethanes having said phosphorate incorporated therewith.

These phosphorates can be simply and efficiently prepared. The use of said phosphorate can greatly improve procedures for preparing flame-retardant polyurethanes and thus may greatly improve their marketability. Significantly, for example, essentially non-scorching flame-retardant flexible polyurethane foams, especially as slabstock, can be prepared. And, flame-retardant polyurethanes which are essentially non-odoriferous can be thus prepared.

ILLUSTRATIVE EMBODIMENTS

The (haloneocarbyl-substituted)(aliphatic or oxyaliphatic)(halogenated aliphatic or oxyaliphatic)phosphorate is a tris(organic)phosphorate. The three organic moieties are apportioned among one haloneocarbyl-substituted, one aliphatic or oxyaliphatic and one halogenated aliphatic or halogenated oxyaliphatic, hydrocarbon moiety.

The haloneocarbyl moiety is a halogen-substituted hydrocarbon or oxyhydrocarbon moiety which contains a neocarbyl moiety. The neocarbyl moiety has a quaternary (i.e., 4°) carbon. The 4° carbon is connectable to the phosphorus through aliphatic carbon to carbon or ether linkages. The neocarbyl moiety is connected to the phosphorus through an oxygen such as in a phosphate ester.

The neocarbyl moiety is more preferably a β-haloneocarbyl moiety. The β-haloneocarbyl moiety is a saturated halogen and carbon-containing moiety which has the 4° carbon bonded directly to a carbon which forms a bond connectable to the phosphorus through an oxygen such as in a phosphate ester. The β-haloneocarbyl moiety is preferably haloalkyl.

Connectable herein means directly or indirectly bonded such as by covalent bonds. Connected herein means directly bonded.

Aliphatic refers to a saturated or unsaturated, nonaromatic hydrocarbon moiety. Oxyaliphatic refers to an aliphatic moiety having at least one ether linkage therein such as, for example, in an ethoxyethyl moiety such as can be incorporated by appropriately employing a carbyloxide such as 2-ethoxyethanol. The oxygens of the phosphorates are not considered an ether linkage. Halogenated aliphatic or oxyaliphatic refers to an aliphatic or oxyaliphatic moiety having at least one halogen substituted, one for one, for hydrogen therein such as, for example, in a 2-chloropropyl-3-(prop-2-en-1-oxy) or 2-chloropropyl-3-(2,3-dibromopropoxy) moiety, or isomeric mixture thereof such as can be incorporated by appropriately employing a carbyloxide such as allyl glycidyl ether, optionally halogenating afterward.

The halogens include fluorine (F), chlorine (Cl), bromine (Br) and iodine (I). Thus, halo moieties include fluoro, chloro, bromo and iodo. Preferred halo moieties are chloro and bromo.

The (haloneocarbyl-substituted)(aliphatic or oxyaliphatic)(halogenated aliphatic or oxyaliphatic)phosphorate is preferably a phosphate ester of the general formula

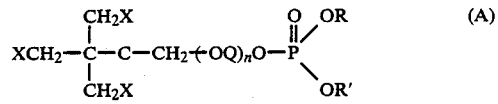

wherein

X is separately at each occurrence hydrogen, halo or $C_{1-5}$ (i.e., from 1 to about 5 carbons) alkyl or $C_{1-5}$ haloalkyl;

Q is separately at each occurrence $C_{2-10}$ (i e., from 2 to about 10 carbons) hydrocarbyl, $C_{3-10}$ oxyhydrocarbyl (i.e., ether-substituted), $C_{3-10}$ halohydrocarbyl or $C_{3-10}$ oxyhalohydrocarbyl;

n is an integer from zero to about 5;

R is $C_{1-10}$ aliphatic or oxyaliphatic, preferably $C_{2-10}$ aliphatic or oxyaliphatic, more preferably $C_{2-10}$ alkyl or oxyalkyl;

R' is $C_{2-10}$ haloaliphatic or oxyhaloaliphatic; but

Q or X contains at least one halo moiety.

Preferably therein,

X is in at least one occurrence a halo moiety, and the remaining X is hydrogen, halo or $C_{1-5}$ haloalkyl, preferably hydro (H) or halo;

Q is $C_{2-4}$ alkyl or $C_{3-4}$ haloalkyl; n is from zero to 2, preferably zero;

R is $C_{2-5}$ alkyl; and

R' is $C_{2-6}$ haloalkyl, more preferably $C_{2-4}$ monohaloalkyl or dihalopropyl.

More preferred haloneocarbyl moieties include those such as $((CH_2Br)_2CH_2Cl)CCH_2{+}OQ{+}_n$; $(CH_2Br(CH_2)_2)CCH_2{+}OQ{+}_n$; $(CH_2Br)_3CCH_2{+}OQ{+}_n$; $(CH_2Cl)_3CCH_2{+}OQ{+}_n$; $((CH_2Br)_2CH_2F)CCH_2{+}OQ{+}_n$; $((CH_2Br)_2CCH_2{+}OQ{+}_n$; $(CH_2Br(CH_2Cl)(CH_3))CH_2{+}OQ{+}_n$; $((CH_2Br)_2C_2H_4Br)CCH_2{+}OQ{+}_n$; $((CH_2Br)_2C_2H_4Cl)CCH_2{+}OQ{+}_n$; $(CH_2Br(CH_2Cl)(C_2H_4Br))CCH_2{+}OQ{+}_n$; $((CH_2Br)_2c_2H_4F)CCH_2{+}OQ{+}_n$; and $((CH_2Br)_2C_2H_5)CCH_2{+}OQ{+}_n$. Most preferred haloneocarbyl moieties are those such as $((CH_2Br)_2CH_2Cl)CCH_2{+}OQ{+}_n$; $(CH_2Br(CH_2Cl)_2)CCH_2{+}OQ{+}_n$; $(CH_2Br)_3CCH_2{+}OQ{+}_n$ and $(CH_2Cl)_3CCH_2{+}OQ{+}_n$, especially $((CH_2Br)_2CH_2Cl)\text{-}CCH_2{+}OQ{+}_n$.

More preferred Q moieties include those such as $C_2H_3(CH_2Cl)$; $C_3H_5Cl$; $c_2H_3(CH_2Br)$; $C_3H_5Br$; $C_2H_3(CH_2F)$; $C_3H_5F$; $C_2H_4$ and $C_2H_3(CH_3)$. Most preferred are Q moieties such as $C_2H_3(CH_2Cl)$; $C_3H_5Cl$; $C_2H_3(CH_2Br)$ and $C_3H_5Br$, especially $C_2H_3(CH_2Cl)$ or $C_2H_3(CH_2Br)$ in combination with $C_3H_5Cl$ or $C_3H_5Br$ (n=2) as $(C_2H_3(CH_2Cl)\text{-})\text{-}(C_3H_5Cl)$; $(C_2H_3(CH_2Br)\text{-}O\text{-}(C_3H_5Cl)$; $(C_2H_3(CH_2cl)\text{-}O\text{-}(C_3H_5Br)$; and $(C_2H_3(CH_2Br)){+}O{+}(C_3H_5Br)$, particularly the Q moiety $(C_2H_3(CH_2Cl)){+}O{+}(C_3H_5Cl)$.

However, n is more preferably zero. Thus, most especially preferred haloneocarbyl moieties include those such as 3-chloro-2,2-bis(bromomethyl)propyl; 3-bromo-2,2-bis(chloromethyl)propyl; 3-bromo-2,2-bis(bromomethyl)propyl; 3-chloro-2,2-bis (chloromethyl)propyl; 3-fluoro-2,2-bis(bromomethyl)propyl and 2,2-bis(bromomethyl)propyl, particularly 3-chloro-2,2-bis(bromomethyl)propyl; 3-bromo-2,2-bis(bromomethyl)propyl and such as (2-(3-bromo-2,2-bis(bromomethyl)propoxy)ethoxy)ethyl.

More preferred R moieties include $C_{2-4}$ alkyl, that is, ethyl; propyl and butyl. Most preferred are $C_{2-4}$ n-alkyl, that is, ethyl; n-propyl and n-butyl.

The more preferred R' moieties include the $C_{2-4}$ monohaloalkyl and $C_3$ dihaloalkyl, that is, dihalopropyl. These moieties include for example, 2-chloroethyl; 2-bromoethyl; etc. and 1,3-dichloropropyl; 1,2-dichloromethylethyl; 3-bromo-1-chloropropyl; 1-bromo-2-chloromethylethyl and so forth.

Thus, preferred (haloneocarbyl-substituted)(aliphatic or oxyaliphatic)(halogenated aliphatic or oxyaliphatic)phosphorates include those such as, for example, ((3-bromo-2,2-bis(methyl)(2-chloroethyl) (ethyl))phosphorate and ((3-bromo-2,2-bis (bromomethyl))(2,3-dichloropropyl)(n-butyl))phosphorate, however, the most preferred are ((3-chloro-2,2-bis (bromomethyl)(2-chloroethyl)(ethyl))phosphorate; ((3-bromo-2,2-bis(bromomethyl)propyl)-(2-chloroethyl) (ethyl))phosphorate; ((2-(3-bromo-2,2-bis (bromomethyl)propoxy)ethoxyethyl)(2-chloroethyl)(ethyl))phosphorate and ((3-bromo-2,2-bis(bromomethyl)propyl) (2,3-dichloropropyl)(ethyl))phosphorate.

The (haloneocarbyl-substituted)(aliphatic or oxyaliphatic)(halogenated aliphatic or oxyaliphatic)phosphorate can be prepared by the process to prepare said phosphorate comprising contacting a carbylphosphorate mono acid halide with a carbyloxide. Conditions are those sufficient to prepare said phosphorate.

The carbylphosphorate mono acid halide is an organic phosphorate which has one of the organic ester moieties substituted with a halide, preferably selected from the group consisting of fluorido, chlorido and bromido. More preferably, the halide of the carbylphosphorate mono acid halide is selected from the group consisting of chlorido and bromido.

Preferably, the carbylphosphorate mono acid halide is of the general formula

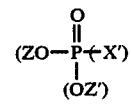

wherein

X' is separately at each occurrence F, Cl or Br, preferably Cl or Br, more preferably Cl;

Z is appropriately selected from the haloneocarbyl moiety or the aliphatic or oxyaliphatic moieties, preferably the foregoing

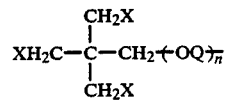

or R moieties; and

Z' is such as Z, provided that Z' and Z are not of the same genera of moieties; for example, with Z haloneocarbyl, Z' can be either the (aliphatic or oxyaliphatic) moiety or the (halogenated aliphatic or oxyaliphatic) moiety.

The carbylphosphorate mono acid halide can be obtained or prepared by known procedures or by a procedure such as disclosed herein. For example, the carbylphosphorate acid halide can be prepared by reacting a phosphorus trihalide such as, for example, phosphorus trifluoride; phosphorus trichloride; phosphorus tribromide with the appropriate monohydroxy alcohols which correspond to the haloneocarbyl or alternate moieties, for example, the aliphatic hydrocarbyl moieties to be bound to the phosphorus as phosphate ester. See, for example, copending U.S. patent application Ser. No. 843,452, filed Mar. 24, 1986 (Attorney Docket No. C-34,970) (incorporated herein by reference). Or, the carbylphosphorate mono acid halide can be prepared by halogenating the appropriate corresponding tris(organic)phosphite. This halogenation can be carried out with halogenating agents such as, for example, elemental fluorine, chlorine, bromine and iodine and bromine chloride, preferably, chlorine and bromine.

The carbyloxide is an oxygen-containing organic compound which appropriately corresponds to the remaining haloneocarbyl, the required (aliphatic or oxyaliphatic) or the (halogenated aliphatic or oxyaliphatic) moieties or suitable parts thereof. Suitable carbyloxides include monohydroxyl alcohols (preferably contacted with the carbylphosphorate acid halide in the presence of an acid acceptor), especially of the general formula ROH with R as defined herein;

oxetanes (preferably contacted with the carbylphosphorate acid halide in the presence of a Lewis acid catalyst) such as, for example, 3-bromoethyl-3-methyloxetane, 3-bromomethyl-3-ethyloxetane, 3,3-bis (chloromethyl)oxetane, 3-(chloromethyl)-3-methyloxetane; and oxiranes, for example, ethylene oxide; 1,2-propylene oxide; epichlorohydrin; epibromohydrin, including neocarbyl-containing oxiranes such as of the general formula

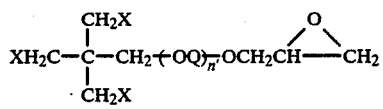

wherein Q and X are as defined herein; n' is an integer from zero to 4, preferably 1. The neocarbyl-containing oxiranes can be prepared by a procedure such as that disclosed by Gibbons, U.S. Pat. No. 3,784,500 (1974) (incorporated herein by reference). The oxiranes are also preferably contacted with the carbylphosphorate acid halide in the presence of the Lewis acid catalyst.

In general, in preparing the (haloneocarbyl-substituted) (aliphatic or oxyaliphatic)(halogenated aliphatic or oxyaliphatic)phosphorate, the carbylphosphorate mono acid halide to carbyloxide equivalent ratio can correspond roughly to a 1:1 equivalent ratio. The ratio is based on the number of equivalents of acid halide in the carbylphosphorate mono acid halide.

Temperatures, in general, can be those employed with the preparation of other organic phosphate esters. Temperatures are preferably from about $-10°$ C. (minus $10°$ C.) to about $120°$ C. Initial contact is preferably carried out at cooler temperatures such as about normal room temperature, for example, $25°$ C., or below. Extended contact time, if desired or necessary, is preferably carried out at elevated temperatures such as about $30°$ C. or above.

Pressures, in general, can be those employed with the preparation of other organic phosphate esters (phosphorates). Preferably, the pressure is ambient pressure.

Times (duration) are those which are sufficient to carry out the preparation. Typical times can be the time it takes for the initial contact to an extended time such as 100 hours or more. Preferably, the time is extended beyond the initial contact for about 1 to 20 hours.

The acid acceptor employed in conjunction with the alcohols can be a compound such as, for example, pyridine, triethylamine or sodium carbonate. The acid acceptor can be added in the appropriate increments to thus accept acid produced by reaction with the carbylphosphorate mono acid halide.

The Lewis acid catalyst employed in conjunction with the neocarbyl-containing oxiranes and oxetanes is preferably a compound such as aluminum tribromide, aluminum trichloride or titanium tetrachloride. Boron trifluoride etherate ($BF_3$-et) is also preferred. For the most part, the Lewis acid catalysts can be employed in amounts from about 1/10 to about 5 percent by weight based on the weight of the carbylphosphorate mono acid halide.

The reaction can be run neat or can employ a diluent. Preferably, a liquid diluent is employed. Preferred liquid diluents include halogenated alkanes such as, for example, methylene chloride, chloroform, carbon tetrachloride and 1,2-dichloroethane.

Preferably, the phosphorates of the invention are prepared by the sequence of the reactions as follows: a neopentyl alcohol such as, for example, 3-chloro-2,2-bis(bromomethyl)propanol; 3-bromo-2,2-bis(bromomethyl)propanol or 3-bromo-2,2-dimethylpropanol is reacted with a phosphorus trihalide, for example phosphorus trichloride, liberating hydrogen halide (e.g., HCl). Next, the resulting dihalophosphite derivative is reacted with an oxirane such as, for example, ethylene oxide, propylene oxide or epichlorohydrin to produce a phosphite. The phosphite is halogenated, for example, chlorinated, at $10°$ C. or colder to produce a halophosphorate, for example, a chlorophosphorate, liberating additionally halogenated organic compound corresponding to the now halogenated moiety released from the phosphite (e.g., 1,2-dichloroethane). This latter general phosphorus compound product is next reacted with an alcohol such as, for example, methanol; ethanol or propanol, preferably ethanol or propanol, in the presence of the acid acceptor, for example, pyridine, triethylamine or potassium carbonate, to produce the desired phosphorate.

Another preferred method for the preparation of these derivatives is the sequence reaction of the neopentyl alcohols previously mentioned with an oxirane in the presence of $BF_3$-etherate. Oxiranes such as ethylene oxide, propylene oxide, epichlorohydrin or allyl glycidyl ether (which is later halogenated) or combination of these are most preferred. Mole ratios are 1 to 4, based on the alcohol. This resulting product is next reacted with phosphites such as trimethyl phosphite, triethyl phosphite or tributyl phosphite, most preferably triethyl phosphite each liberating an alcohol. The resulting product is next halogenated, for example, chlorinated, at $10°$ C. or lower, liberating halogenated organic, for example, 1-chloroethane, and the resulting product is reacted with an oxirane such as those mentioned above in the presence of a Lewis acid catalyst such as $TiCl_4$ or $AlCl_3$ to produce the desired product.

The (haloneocarbyl-substituted)(aliphatic or oxyaliphatic)(halogenated aliphatic or oxyaliphatic)phosphorate is preferably purified by procedures generally analogous to those in Birum et al., U.S. Pat. No. 3,132,169 (1964) (incorporated herein by reference), for example, by a neutral or basic aqueous wash of the (halo- neocarbyl-substituted)(aliphatic or oxyaliphatic) (halogenated aliphatic or oxyaliphatic)phosphorate product. A dilute acid wash of the product can be employed, preferably with an aqueous mixture of the acid, especially with employment of catalysts such as $AlCl_3$. The dilute acid wash is a most preferred step. The product mixture ratio is typically not changed by the dilute acid wash. Purification by distillation is an additionally preferred step.

The process can prepare an extremely pure product which contains little or no undesired phosphorate by-products. Preferably, the desired (haloneocarbyl-substituted)(aliphatic or oxyaliphatic)(halogenated aliphatic or oxyaliphatic)phosphorate is 90 percent free of other phosphorate by-products, or more pure, as determined by gas chromatographic methods (e.g., capillary), more preferably about 95 percent or more pure, and most preferably, 99 percent or more pure.

The (haloneocarbyl-substituted)(aliphatic or oxyaliphatic)(halogenated aliphatic or oxyaliphatic)phosphorate may be a low viscosity liquid such as is indicated by Brookfield viscosity. The Brookfield viscosity herein is the viscosity measured at $25°$ C. on a Brookfield viscometer with a number 6 spindle rotating at 100 rotations per minute (rpm) submersed with sample in the center of a sample vessel with a width at least 125 percent of the spindle diameter.

Preferably, the Brookfield viscosity of the (haloneocarbyl-substituted)(aliphatic or oxyaliphatic)-(halogenated aliphatic or oxyaliphatic)phosphorate product is about 10,000 centipoise (cP) or below at 25° C., more preferably about 5,000 cP or below and most preferably about 2,500 cP or below. It is especially preferred that the Brookfield viscosity of the product at 25° C. is about 1,000 cP or below.

Preferably, the (haloneocarbyl-substituted)(aliphatic or oxyaliphatic)(halogenated aliphatic or oxyaliphatic)-phosphorate has high thermal stability. One preferred method to measure this is by thermogravimetric analysis (i.e., TGA), where the sample tested is continuously monitored for weight loss as its temperature is progressively increased in an oven with a nitrogen atmosphere. The progressive temperature increase is at a rate of 20° C. per minute from an intitial temperature of 20° C. with the sample size initially between 0.010 g and 0.020 g. Under these test conditions, thermogravimetric analyses preferably have a 50 percent weight loss of sample (TGA$_{50}$) at a temperature of about 200° C. or above, more preferably about 230° C. or above and most preferably about 250° C. or above.

The thermogravimetric analysis at 10 percent weight loss (TGA$_{10}$) can be used also. The TGA$_{10}$ is otherwise measured as is the TGA$_{50}$. Preferred TGA$_{10}$ values include values found at about 160° C. or above, more preferably about 180° C. or above and most preferably about 200° C. or above.

In general, the (haloneocarbyl-substituted) (aliphatic or oxyaliphatic)(halogenated aliphatic or oxyaliphatic)-phosphorate can be employed as a component in flame-retardant polurethanes. Amounts thus employed are preferably those sufficient to render the polyurethane flame-retardant, such as in amounts from about ½ to 50 percent by weight of other polyurethane components, for example, in amounts from about 5 to 20 percent by weight of polyahl of a foam. The use can typically satisfy at least one production characteristic of the polyurethanes.

The polyurethanes of this invention comprise organic polyisocyanates, polyahls and flame-retardant amounts of the phosphorate compounds of this invention. The polyahls are organic compounds with at least two active hydrogen moieties such as determined by the Zerewitinoff test (see, e.g., Kohler et al., *J. Am. Chem. Soc.*, 49, 3181–88 (1927)) and with an average molecular weight of at least about 60 g per mole. See, for example, Rosenkranz et al., U.S. Pat. No. 3,928,299 (1975) (incorporated herein by reference) for compounds otherwise known which may thus be considered polyahls. The polyurethanes can be prepared by known methods such as disclosed by Hoppe et al., U.S. Pat. No. Re 24,514 (reissued 1958) (incorporated herein by reference). The foams may also be prepared by the froth technique as described by Dunlap et al. in U.S. Pat. No. 3,755,212 (1973); by Barron et al. in U.S. Pat. No. 3,821,130 (1974); and by Walters et al. in U.S. Pat. No. 3,849,146 (1974) which are also incorporated herein by reference. The most preferred technique is the "one-shot" technique, where all the reactants are added simultaneously at the time of foaming, because it is generally used to prepare flexible polyurethane foams. Most, if not all, modern flexible slabstock (continuous) polyurethane foam machines are designed on the basis of this approach.

Of the polyahls, polyols are preferred. Preferred polyols include triol polyether polyols with equivalent weights from about 500 to 2,500 and blends of triols and diols with overall active hydrogen functionality of from about 2½ to 3. See, for example, Baggett et al., U.S. Pat. No. 2,871,219 (1959); Smith, U.S. Pat. No. 2,891,073 (1959); Pannell, U.S. Pat. No. 3,058,921 (1962) (each incorporated herein by reference).

Especially preferred polyisocyanates include a mixture of 80 percent by weight 2,4-toluene diisocyanate with 20 percent by weight 2,6-toluene diisocyanate (generally known as TDI 80/20 or T-80) and a mixture of 65 percent by weight 2,4-toluene diisocyanate with 35 percent 2,6-toluene diisocyanate (TDI 65/35 or T-65). These are typically used in flexible polyurethane foams. The TDI 80/20 is more preferred.

Also preferred are pure and polymeric methylene-4,4'-diphenyldiisocyanate (MDI). The MDI types are typically used in rigid polyurethane foams.

Other components can be present in the preparation of the polyurethanes, especially the foams, as is generally known in the art. For example, catalysts such as nitrogenous catalysts such as amino compounds, for example, those disclosed by McEntire, U.S. Pat. No. 4,101,470 (1978); Zimmerman et al., U.S. Pat. No. 4,433,170 (1984); Jachimowicz, U.S. Pat. No. 4,450,246 and Zimmerman et al., U.S. Pat. No. 4,464,488 (1984) (each incorporated herein by reference) can be employed with other catalysts such as tin compounds including those such as stannous chloride and tin salts of carboxylic acids such as, for example, stannous octoate and dibutyltin di-2-ethylhexanoate, as well as other organometallic compounds such as disclosed by Brachhagen et al., U.S. Pat. No. 2,846,408 (1958) (incorporated herein by reference). Also, a wetting agent or surface-active agent can be employed, especially in preparing high grade foams, preferably a silicone containing organic compound or block polyethers of propylene glycol prepared with ethylene oxide and propylene oxide. Also, a chain-extending agent, which is a compound with at least two active hydrogens per molecule such as, for example, 1,2-diaminoethane; (R.)-1,2-dimethylaminopropane; 2-aminoethanol; ethylene glycol; L-alanine and preferably water can be employed. Also, especially in the preparation of the foamed polyurethanes, an auxiliary blowing agent preferably such as a volatile haloalkane, for example, trichlorofluoromethane, can be employed.

Preferred flexible polyurethane foam formulations with which the (haloneocarbyl-substituted)(aliphatic or oxyaliphatic)(halogenated aliphatic or oxyaliphatic)-phosphorates are incorporated as a flame retardant include compositions such as follows:

| Reactant | Concentration (pph) |
| --- | --- |
| polyol | 100 |
| TDI index | 80–120 |
| flame retardant | 6–18 |
| water | 1.0–5.5 |
| silicone surfactant | 0.2–3 |
| tertiary amine catalyst | 0.02–2 |
| auxiliary blowing agent | 0.5–40 |
| tin catalyst | 0.05–0.5 |

Also, flexible foams with densities from about 1.0 pound per cubic foot (i.e., about 16 kg per m$^3$) to about 4.0 pounds per cubic foot (i.e., about 64 kg per m$^3$) are preferred.

The polyurethane production characteristic(s) which is (are) satisfied, or even improved, by the method of this invention, is preferably selected from the group consisting of (1) processability;
(2) scorch;
(3) odor; and
(4) flame-retardant efficiency.

Processability is a production characteristic which can be satisfied or improved. A preferred measure of the processability is the Brookfield viscosity.

Processability difficulties for higher viscosity flame-retardant compounds may be reduced by the use of diluents such as non-halogenated phosphate ester compounds. Preferably, such diluents are not used in processing.

Scorch is a production characteristic which may be satisfied or improved by being reduced to minimal levels or even eliminated. A preferred measure of scorch (discoloration) is a $\Delta E$ in National Bureau of Standards (i.e., NBS) units by the Hunter Colorimeter test of about 10 or below, more preferably about 6 or below and most preferably about 4 or below, or, particularly in a laboratory scale test, after inducing scorch by the Wampfler-Fielding procedure described in U.S. patent application Ser. No. 856,523, filed Apr. 28, 1986 (Attorney Docket No. C-35,122) (incorporated herein by reference), comparable Hunter test $\Delta E$ values of about 20 or below; 10 or below; 8 or below.

The Hunter test differs from the known Gardner Colorimeter test in that in the Hunter test, the color of both the sample set and control set are compared to the color of a standard pure white tile. The standard white tile may contain pure white MgO. If the sample versus control difference is determined by subtraction (i.e., sample-control) after this comparison to the tile, the values of the Hunter test are typically substantially equivalent to values determined by the Gardner test. The Gardner Colorimeter test is more completely described in Albright et al., U.S. Pat. No. 4,083,825 (1978) from column 8, line 58 to column 11, line 23 (which material is incorporated herein by reference).

The most preferred polyurethane foam sample for the Hunter Colorimeter test, especially with flexible foams, is a representative sample taken from a large-scale commercial production bun. The bun is cross-sectioned and the whole large-scale cross-section of bun is tested for scorch in the minimum number of required 4.0 square-inch (26 cm$^2$) cross-sections (2.0 inches $\times$ 2.0 inches; 5.1 cm $\times$ 5.1 cm), and each smaller-scale $\Delta E$ value is summed, and the summation is divided by the required number of 4.0 square-inch cross-sections. This is the average $\Delta E$ value of the large-scale sample. The sample is 2.0 inches (2.5 cm) in height. Thus, the sample is a cube of 2.0 inches per side.

As an indicia of scorch resistance when incorporated into a polyurethane, especially in a flexible foam, the thermal stability properties of the phosphorate flame-retardant compounds may be used.

Odor is a production characteristic which may be satisfied or improved by being reduced or even eliminated. The presence of a halogenated neopentane, for example, tetrabromoneopentene, at levels of about 1–4 percent by weight, may cause the odor. Keeping the presence of such a halogenated neopentane to levels below 1 percent by weight, more preferably 0.5 percent by weight, typically eliminates such an odor in the resulting flame-retardant polyurethane, especially in slab-stock foam. The instant process typically does not produce such an odoriferous halogenated neopentane.

Flame-retardant efficiency is a production characteristic which may be satisfied or improved. By flame-retardant it is meant that the phosphorate, when incorporated into the polyurethane, reduces the propensity of the polyurethane to propagate combustion after the removal of a small-scale ignition source such as a lit Bunsen burner. The flame-retardant efficiency in additive-type flame-retardant phosphorus compounds incorporated with polyurethanes is typically a function of phosphorus-halogen content. Broiminated compounds are preferred. A higher bromine content increases the flame-retardant efficiency by its mere presence within the composition. Also, thus, the lower alkyl ester compounds are preferred. The $C_{2-4}$ alkyl esters are most preferred because the methyl ester has a tendency to hydrolyze more easily and thus cause a humid aging problem.

One preferred method to measure this flame-retardant efficiency is an oxygen index (i.e., limiting oxygen index) measured by the oxygen demand test of ANSI/ASTM D-2863-77 (ASTM American National Standard) wherein the minimum concentration of oxygen in a mixture of dry $O_2$ and dry $N_2$ flowing upward, needed to cause combustion in a standard test column that will just support combustion under equilibrium conditions of candle-like burning is measured. Other conditions of the ANSI/ASTM D-2863-77 oxygen demand test include those set out in the ASTM American National Standard test (incorporated herein by reference).

Preferably, for ten appropriate A through D type (as in the D-2863-77 standard) specimens with the flame-retardant composition, the average limiting oxygen index (i.e., average LOI) is raised 10 percent or more, more preferably 20 percent or more and most preferably 30 percent or more, when measured either by time until extinguishing of the flame or distance of the burned specimen according to ASTM D-2863-77, when compared to ten otherwise comparable specimens without the flame-retardant composition. It is also preferred that the average LOI of ten appropriate A through D type specimens is raised to above 21, more preferably to about 25 or above and most preferably, to about 30 or above.

When incorporated into a rigid polyurethane foam, such as an insulating foam, preferred measures include the Steiner tunnel test of ASTM E-84 or the equivalent such as Underwriter's Laboratories 723. It is preferred that the rigid foam pass the E-84 test or equivalent with a Class II rating or better. It may be desired to incorporate into the flame-retardant composition an amount effective to secure a Class I rating. Other tests such as the German DIN-4102-B2 test or its Swiss counterpart may be used.

When incorporated into a flexible polyurethane foam as a flame retardant, a preferred measure of the flame-retardant efficiency of the flame-retardant foam composition is the two-part California 117 test (i.e., both of the Vertical Burn tests and the Smoldering test) as in California Technical Bulletin 117, State of California Department of Consumer Affairs Bureau of Home Furnishings, North Highlands, California (January, 1980) (which is incorporated herein by reference). It is preferred that the two-part California 117 test is passed by the flame-retardant flexible foam composition.

In each of the foregoing, it is preferred that the flame-retardant efficiency be substantially retained after aging. A preferred measure of this retention may be obtained by subjecting the flame-retardant polyurethane to elevated temperature (e.g., 104° C.) aging in a circulating air oven for 24 hours, followed by passing the requirements of the foregoing flame-retardant efficiency tests, such as in the case of a flexible foam by passing the California 117 Vertical Burn test.

Reduction of scorch and odor are each, and especially in combination, of high priority. Reduction of problems due to odor and processability or scorch and processability are also desirable. Reduction of each of the problems due to processability, scorch, odor and loss of flame-retardant efficiency is most desired.

Preferably, the method of employing the (haloneopentyl-substituted)(aliphatic or oxyaliphatic)-(halogenated aliphatic or oxyaliphatic)phosphorate as a flame retardant is generally akin to the method disclosed in the referenced copending U.S. patent application Ser. No. 856,523, filed Apr. 28, 1986.

Specific Embodiments

The following examples further illustrate the invention. Parts and percentages are by weight unless otherwise specified.

EXAMPLE 1

Preparation of phosphoric acid: ethyl, chloroethyl, (2-(3-bromo-2,2-bis(bromomethyl)propoxy)ethyl)ester of the following general formula (E4) by the following general sequence

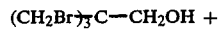

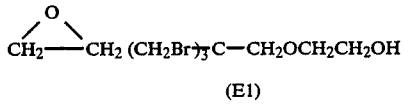

(E1)

E1 +

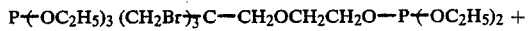

(E2)

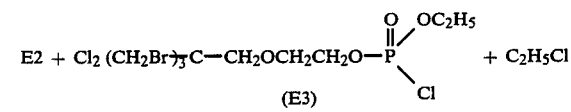

(E3)

E3 +

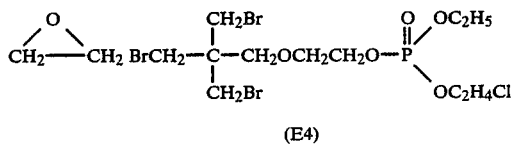

(E4)

A. Preparation of the mono acid halide

Into a flask are placed 65.5 g of 3-bromo-2,2-bis(bromomethyl)propanol (0.2 mole), 200 ml of methylene chloride and 1 ml of BF$_3$-et. This mixture is stirred until a solution is obtained. A solution of 8.8 g of ethylene oxide (0.2 mole) in 25 ml of methylene chloride is added dropwise. Upon completion of reaction, 5 g of sodium carbonate is added, and the mixture is stirred. The insoluble matter is filtered off, and the liquid phase is heated to 80° C. at 1-2 mm Hg (0.133–0.266 kPa) until low boilers cease to distill off. The mixture is allowed to cool, and 36 g of triethyl phosphite and 2 g of sodium ethylate are added. This mixture is stirred and is slowly heated to 120° C. while the low boiling by-product, ethanol, distills off. At the time ethanol ceases to distill off, the reaction mixture is placed under reduced pressure and is allowed to cool. The resulting oil containing E2 is taken up in 200 ml of methylene chloride and is cooled to 10° C. in an ice water bath. Next, 16 g of chlorine is bubbled into the reaction mixture. Next, the mixture is stirred until completion of reaction as is indicated by absence of chlorine color. The mixture contains E3.

B. Preparation of the title phosphate (E4)

Next, 1 g of AlCl$_3$ is added, and a solution of 10 g ethylene oxide in 50 ml of methylene chloride is added dropwise. Upon completion of this addition, the mixture is heated to reflux for 30 minutes, and some of the low boilers are distilled off. The mixture is allowed to cool, and 100 g of dilute (1N) aqueous HCl solution is added. The product phase is separated and is stirred with another 100 ml of the dilute HCl, is separated, is stirred with a mixture of 5 g of sodium carbonate and 30 g of sodium sulfate, is filtered, and solvent is distilled off at 80° C. and under 1-2 mm Hg pressure to produce 79 g of an oil (73 percent yield). The oil has a Brookfield viscosity (No. 6 spindle; 100 rpm; 25° C.) of 750 cP and a TGA$_{10}$ of 202° C.; TGA$_{50}$ of 256° C.

EXAMPLE 2

Preparation, scorch inducement and evaluation of flexible polyurethane foams

A. Preparation

If a flexible polyurethane foam is prepared as follows, the foam has an isocyanate index of 110.

First, the A-side (isocyanate side) is weighed out into a half-cup (118 ml) glass jar and set aside. The A-side is 62.3 g of Voranate* T-80 (*Trademark of The Dow Chemical Company), a mixture of toluene-2,4- and 2,6-diisocyanates in a weight ratio of toluene-2,4-diisocyanate to toluene-2,6-diisocyanate of about 80:20.

Next, the B-side (polyahl side) is weighed out and is placed, in the numerical sequence listed, into a one-quart (946 ml) paper cup set beside the set aside A-side.

| B-Side Component | (g) Weight |
|---|---|
| Voranol* 3137 (*Trademark of The Dow Chemical Co.) (a polyether polyol with a hydroxyl number of about 53.4) | 100.0 |
| Sample FR (phosphorate separately of Example 1 or Thermolin ® (Olin Chemical Co.) (comparative)) | 10.0 |
| Water | 5.0 |
| Q-25125 (silicone surfactant available from The Dow Corning Corp.) | 1.0 |
| Methylene chloride | 6.0 |
| NIAX ™ A200 (amine catalyst available from Union Carbide) | 0.30 |
| T-10 (50% solution of stannous octoate available from M&T Chemical) | 0.60 |

Next, the B-side is mixed with a high speed electric drill-powered stirrer for 15 seconds. Next, the A-side is immediately added, and immediately mixed with the drill-stirrer for 5 seconds.

The A-B mixture is immediately poured into an 83-ounce (2.45-liter) clean cardboard bucket, and the resultant foam is allowed to rise, the bucket being in upright position in an upright 5-gallon (18.9-liter) pail, the bucket disjointed from and above the surface of ½ gallon of water in the pail.

B. Scorch inducement by the Wampfler-Fielding procedure

Following "blow-off" the lid of the pail containing the water is put into place and the covered pail containing the bucket is placed in a 160° C. oven for one hour. The relative humidity in the covered pail is thus approximately 100 percent. Next, the bucket with foam is removed from the pail, and the foam is allowed to cool to room temperature at ambient conditions in the bucket.

The foregoing severe conditions are employed to attempt to induce scorch because generally humid conditions are a cause of scorch (discoloration), especially in flexible foams and particularly in those with phosphorus- or halogen-containing components. The high temperature and the time duration are employed because of their resemblance to the conditions which can accompany commercial scale production of foamed polyurethanes, especially flexible slabstock. Overall, the induced conditions are more severe than typically encountered in polyurethane foam production.

C. Evaluation

A two-inch (5.08-cm) cross-sectional slice is cut off near the top of each foam sample. Next, a two-inch section is cut from the middle of each cross-sectional slice. The underside of this section is used for color determination.

Color is measured on a Macbeth Colorimeter using the Hunter Color Scale. The Hunter Color Scale compares the color of the sample to a standard white tile.

Three measurements are made for each sample and then averaged. The average delta E value ($\Delta E$) for each sample is then compared to the average $\Delta E$ value determined by the Hunter Color Scale for an otherwise equivalent foam sample section containing no flame retardant. A value ($\Delta E(FOAM)$) is calculated according to the following equation.

$$\Delta E(FOAM) = \Delta E(SAMPLE) - \Delta E(NO\ FR\ FOAM)$$

The following is obtained.

| SAMPLE FR | $\Delta E$ | $\Delta E(FOAM)$ |
|---|---|---|
| Example 1 | about 18 | about 11 |
| Thermolin ® 101 | | |
| None | 7.0 | — |

The $\Delta E(FOAM)$ values as are obtained with the SAMPLE FR of Example 1 are comparable to or even sometimes better than the value as is obtained with the comparative SAMPLE FR. The comparative (Thermolin ® 101) is typically sold as a substantially non-scorching flame retardant. Thus, the (haloneocarbyl-substituted)(aliphatic or oxyaliphatic)(halogenated aliphatic or oxyaliphatic)phosphorates are at least substantially, even essentially, non-scorching flame retardants for polyurethanes.

The foams are flame-retardant. The foam with SAMPLE FR of Example 1 generally passes requirements of the California 117 test. The foam with the SAMPLE FR of Example 1 is at least substantially non-odoriferous.

EXAMPLE 3

Commercial-type production

If, by the one-shot technique, a commercial-type scale slabstock flexible polyurethane foam with about 110 isocyanate index is prepared with about 10 pph of the phosphorate of Example 1 incorporated therein, the foam is easily processable and is flame-retardant. In addition, the foam exhibits high flame-retardant efficiency, passing the California 117 test as set out by the California 117 test requirements, is essentially non-scorching and is substantially non-odoriferous.

We claim:

1. A method for satisfying a production characteristic of a flame-retardant polyurethane comprising incorporating a (haloneocarbyl-substituted) (aliphatic or oxyaliphatic)(halogenated aliphatic or oxyaliphatic)phosphorate into a polyurethane whereby said production characteristic is satisfied.

2. The method of claim 1 wherein said production characteristic is selected from the group consisting of processability; scorch; odor and flame-retardant efficiency.

3. The method of claim 2 whereby said production characteristic is improved, and the polyurethane is a flexible slabstock foam.

4. A process to prepare a flame-retardant polyurethane comprising reacting a polyahl with an organic isocyanate in the presence of a (haloneocarbyl-substituted)(aliphatic or oxyaliphatic)(halogenated aliphatic or oxyaliphatic)phosphorate.

5. The process of claim 4 wherein the polyurethane is a flexible foam, and said phosphorate is selected from the group consisting of ((2-(3-chloro-2,2-bis (bromomethyl)propoxy)ethyl)(chloroethyl)(ethyl)phosphorate and ((2-(3-bromo-2,2-bis(bromomethyl)propoxy)ethyl)(chloroethyl)(ethyl))phosphorate.

6. Flame-retardant polyurethanes having a (haloneocarbyl-substituted)(aliphatic or oxyaliphatic)-(halogenated aliphatic or oxyaliphatic)phosphorate incorporated therewith.

7. The composition of claim 6 which is substantially non-scorching and non-odoriferous.

8. The composition of claim 7 which is a flexible foam.

9. The composition of claim 8 which is a slabstock flexible foam.

10. The composition of claim 8 which passes the California 117 flame-retardant test.

11. The composition of claim 9 which passes the California 117 flame-retardant test.

12. The composition of claim 11 wherein said phosphorate is ((2-(3-chloro-2,2-bis(bromomethyl) propoxy)ethyl)(chloroethyl)(ethyl))phosphorate and ((2-(3-bromo-2,2-bis(bromomethyl)propoxy)ethyl)(chloroethyl)(ethyl))phosphorate.

* * * * *

UNITED STATES PATENT AND TRADEMARK OFFICE
CERTIFICATE OF CORRECTION

Page 1 of 2

PATENT NO. : 4,945,118

DATED : July 31, 1990

INVENTOR(S) : Chester E. Pawloski et. al

It is certified that error appears in the above-identified patent and that said Letters Patent is hereby corrected as shown below:

Column 3, line 6 "($CH_2Br(CH_2)_2)CCH_2$" should correctly read --($CH_2Br(CH_2Cl)_2)CCH_2$--.

Column 3, line 8 "(($CH_2Br)_2CCH_2$" should correctly read --(($CH_2Br)_2CH_3)CCH_2$--.

Column 3, line 12 "(($CH_2Br)_2C_2H_4F)CCH_2$" should correctly read --(($CH_2Br)_2C_2H_4F)CCH_2$--.

Column 3, line 20 "$C_2H_3(CH_2Br);$" should correctly read --$C_2H_3(CH_2Br);$--.

Column 3, line 25 "($C_2H_3(CH_2Cl)$—)—($C_3H_5Cl$);" should correctly read --($C_2H_3(CH_2Cl)$)-O-($C_3H_5Cl$);--.

Column 3, line 26 "($C_2H_3(CH_2Br)$—O—($C_3H_5Cl$);" should correctly read --($C_2H_3(CH_2Br)$)-O-($C_3H_5Cl$);--.

Column 3, line 27 "($C_2H_3(CH_2Cl)$—O—($C_3H_5Br$);" should correctly read --($C_2H_3(CH_2Cl)$)-O-($C_3H_5Br$);--.

Column 10, line 12 "Broiminated" should correctly read --Brominated--.

UNITED STATES PATENT AND TRADEMARK OFFICE
CERTIFICATE OF CORRECTION

PATENT NO. : 4,945,118

DATED : July 31, 1990

INVENTOR(S) : Chester E. Pawloski et. al

It is certified that error appears in the above-identified patent and that said Letters Patent is hereby corrected as shown below:

Column 13, line 51, the table under "SAMPLE FR" should appear as follows:

| SAMPLE FR | $\Delta E$ | $\Delta E(FOAM)$ |
|---|---|---|
| | about | about |
| Example 1 | 18 | 11 |
| Thermolin ® 101 | 18 | 11 |
| None | 7.0 | — |

Column 14, line 42 "(chloroethyl)(ethyl)phosphorate" should correctly read --(chloroethyl)(ethyl))phosphorate--.

Signed and Sealed this

Second Day of June, 1992

Attest:

DOUGLAS B. COMER

Attesting Officer

Acting Commissioner of Patents and Trademarks